(12) United States Patent
Wolff et al.

(10) Patent No.: US 7,507,722 B1
(45) Date of Patent: Mar. 24, 2009

(54) INTRAVASCULAR DELIVERY OF NUCLEIC ACID

(75) Inventors: Jon A. Wolff, Madison, WI (US); Vladimir G. Budker, Middleton, WI (US)

(73) Assignee: Roche Madison Inc., Madison, WI (US)

( * ) Notice: Subject to any disclaimer, the term of this patent is extended or adjusted under 35 U.S.C. 154(b) by 0 days.

(21) Appl. No.: 09/707,000

(22) Filed: Nov. 6, 2000

Related U.S. Application Data (60) Provisional application No. 60/163,719, filed on Nov. 5, 1999.

(51) Int. Cl.
*A01K 43/04* (2006.01)
*A61K 31/715* (2006.01)

(52) U.S. Cl. ........................................ 514/44; 424/93.2

(58) Field of Classification Search .................. 514/44; 424/93.1, 93.2, 93.21
See application file for complete search history.

(56) References Cited

U.S. PATENT DOCUMENTS

| | | | | |
|---|---|---|---|---|
| 5,521,291 | A | 5/1996 | Curiel | 530/391.7 |
| 5,580,859 | A | 12/1996 | Felgner | 514/44 |
| 5,583,020 | A | 12/1996 | Sullivan | 435/172.3 |
| 5,693,622 | A * | 12/1997 | Wolff et al. | |
| 5,698,531 | A | 12/1997 | Nabel | 514/44 |
| 5,910,488 | A * | 6/1999 | Nabel et al. | |
| 5,922,687 | A | 7/1999 | Mann | 514/44 |
| 6,265,387 | B1 * | 7/2001 | Wolff et al. | |
| 6,379,966 | B2 * | 4/2002 | Monahan et al. | |
| 6,495,131 | B1 * | 12/2002 | Draijer-van der Kaaden et al. ........................................... | 424/93.2 |

OTHER PUBLICATIONS

Deonarain et al. Ligand-targeted receptor-mediated vectors for gene delivery pp. 53-69 1998.*
Crystal Transfee of genes to humans: early lessons and obstacles to success vol. 270, p. 404-410 1995.*
Verma et al. Gene therapy promises, problems and prospects pp. 239-242 vol. 389 1997.*
Miller et al. Targeted vectors for gene therapy pp. 109-199 vol. 9 1995.*
Sferra et al. Gene transfer to the intestinal tract: a new approach using selective injection of the superior mesenteric artery pp. 681-687 1997.*
Milas et al. Isolated limb perfusion in the sarcom-bearing rat: a novel preclinical gene delivery system1 vol. 3, p. 2197-2203 1997.*
Ye et al. liver bypass significantly increases the transduction efficiency of recombinant adenoviral vectors in the lung, intestine, and kidney pp. 621-627 2000.*
Zhang et al. efficient expression of naked DNA delivered intraarterially to limb muscles of nonhuman primates pp. 427-438 2001.*
Atlas of Human Anatomy (Netter, ed. Novartis, 1989) Plates 416-422.*
Boulikas, Teni, "Gene Therapy to Human Diseases: Ex Vivo and In Vivo Studies (Review)." *International Journal of Oncology*; 1996; vol. 9; pp. 1239-1251.
Budker, V., Et al., "The Efficient Expression of Intravascularly Delivered DNA in Rat Muscle." *Gene Therapy*; 1998; vol. 5; pp. 272-276.
French, Brent A., Et al., "Cellular and Molecular Cardiology: Percutaneous Transluminal In Vivo Gene Transfer by Recombinant Adenovirus in Normal Porcine Coronary Arteries, Atherosclerotic Arteries, and Two Models of Coronary Restenosis." *Circulation*; Nov. 1994; vol. 90(5); pp. 2402-2413.
Rekhter, Mark D. MD, Phd, Et al., "Graft Permeabilization Facilitates Gene Therapy of Transplant Arteriosclerosis in a Rabbit Model." *Circulation*; Sep. 29, 1998; vol. 98(13); pp. 1335-1341.
Rekhter, Mark D., Et al., "Gene Transfer Into Normal and Atherosclerotic Human Blood Vessels." *Circ. Res.*; 1998; vol. 82; pp. 1243-1252.
Ross, Gail, Et al., "Gene Therapy in the United States: A Five-Year Status Report." *Human Gene Therapy*; Sep. 10, 1996; vol. 7; pp. 1781-1790.
Simari, Robert D., Et al., "Regulation of Cellular Proliferation and Intimal Formation Following Balloon Injury in Atherosclerotic Rabbit Arteries." *Gene Therapy for Atherosclerotic Arteries; J. Clin. Invest.*; Jul. 1996; vol. 98, No. 1; pp. 225-235.
Von Der Leyen, Heiko, E., Et al., "A Pressure-Mediatated Nonviral Method For Efficient Arterial Gene and Oligonucleotide Transfer." *Human Gene Therapy*; Sep. 20, 1999; vol. 10; pp. 2355-2364.
Zhang, Guofeng, Et al., "Expression of Naked Plasmid DNA Injected into the Afferent and Efferent Vessels of Rodent and Dog Livers." *Human Gene Therapy*; Oct. 10, 1997; vol. 8; pp. 1763-1772.

* cited by examiner

*Primary Examiner*—Michael C. Wilson
(74) *Attorney, Agent, or Firm*—Mark K. Johnson; Kirk Ekena (57) ABSTRACT

Disclosed is a process for transfecting genetic material into a mammalian cell to alter endogenous properties of the cell. The process comprises designing a polynucleotide for transfection. Then the polynucleotide is inserted into a mammalian blood vessel. Prior to insertion, subsequent to insertion, or concurrent with insertion the permeability of the vessel is increased using an exterior cuff thereby the genetic material is delivered to the parenchymal cell.

29 Claims, 3 Drawing Sheets

INTRAVASCULAR DELIVERY OF NUCLEIC ACID

CROSS-REFERENCE TO RELATED APPLICATIONS

Provisional Application Ser. No. 60/163,719 Filing Date Nov. 5, 1999.

FEDERALLY SPONSORED RESEARCH

N/A

FIELD

The invention relates to compounds and methods for use in biologic systems. More particularly, processes that transfer nucleic acids into cells are provided. Nucleic acids in the form of naked DNA or a nucleic acid combined with another compound are delivered to cells.

BACKGROUND

Biotechnology includes the delivery of a genetic information to a cell to express an exogenous nucleotide sequence, to inhibit, eliminate, augment, or alter expression of an endogenous nucleotide sequence, or to express a specific physiological characteristic not naturally associated with the cell. Polynucleotides may be coded to express a whole or partial protein, or may be anti-sense, or non-viral DNA, or recombine with chromosomal DNA.

A basic challenge for biotechnology and thus its subpart, gene therapy, is to develop approaches for delivering genetic information to cells of a patient in a way that is efficient and safe. This problem of "drug delivery," where the genetic material is a drug, is particularly challenging. If genetic material are appropriately delivered they can potentially enhance a patient's health and, in some instances, lead to a cure. Therefore, a primary focus of gene therapy is based on strategies for delivering genetic material in the form of nucleic acids. After delivery strategies are developed they may be sold commercially since they are then useful for developing drugs.

Delivery of a nucleic acid means to transfer a nucleic acid from a container outside a mammal to near or within the outer cell membrane of a cell in the mammal. The term transfection is used herein, in general, as a substitute for the term delivery, or, more specifically, the transfer of a nucleic acid from directly outside a cell membrane to within the cell membrane. The transferred (or transfected) nucleic acid may contain an expression cassette. If the nucleic acid is a primary RNA transcript that is processed into messenger RNA, a ribosome translates the messenger RNA to produce a protein within the cytoplasm. If the nucleic acid is a DNA, it enters the nucleus where it is transcribed into a messenger RNA that is transported into the cytoplasm where it is translated into a protein. Therefore if a nucleic acid expresses its cognate protein, then it must have entered a cell. A protein may subsequently be degraded into peptides, which may be presented to the immune system.

It was first observed that the in vivo injection of plasmid DNA into muscle enabled the expression of foreign genes in the muscle (Wolff, J A, Malone, R W, Williams, P, et al. Direct gene transfer into mouse muscle in vivo. *Science* 1990; 247: 1465-1468.). Since that report, several other studies have reported the ability for foreign gene expression following the direct injection of DNA into the parenchyma of other tissues. Naked DNA was expressed following its injection into cardiac muscle (Acsadi, G., Jiao, S., Jani, A., Duke, D., Williams, P., Chong, W., Wolff, J. A. Direct gene transfer and expression into rat heart in vivo. The New Biologist 3(1), 71-81, 1991.).

SUMMARY

In one preferred embodiment, a process is described for delivering a polynucleotide into a parenchymal cell of a mammal, comprising making a polynucleotide such as a nucleic acid. Then, inserting the polynucleotide into a mammalian vessel, such as a blood vessel and increasing the permeability of the vessel. Finally, delivering the polynucleotide to the parenchymal cell thereby altering endogenous properties of the cell. Increasing the permeability of the vessel consists of increasing pressure against vessel walls and/or inhibiting the flow of the vessel fluid.

In another preferred embodiment, an in vivo process for delivering a polynucleotide to a parenchymal cell of a mammal is described. First, the polynucleotide is inserted into a blood vessel. Then, interior blood flow is externally impeded and the naked DNA is delivered to the parenchymal cell. The polynucleotide may consist of naked DNA, a viral particle/vector, a non-viral vector or may be a blocking polynucleotide for preventing gene expression. The parenchymal cell may consist of a muscle cell, such as a limb (leg or arm) muscle cell.

The process includes externally impeding interior blood flow by externally applying pressure to interior blood vessels such as compressing mammalian skin by applying a tourniquet over the skin. Compressing mammalian skin also includes applying a cuff over the skin such as a sphygmomanometer.

In another preferred embodiment, an in vivo process for delivering a polynucleotide to a mammalian cell, consists of inserting the polynucleotide into a blood vessel and applying pressure to the blood vessel. The pressure is applied externally to mammalian skin and the polynucleotide is delivered to the mammalian cell. However, it is important that the full function of the mammal's limbs subsequent to delivery is maintained using this process. The process especially consists of a polynucleotide delivered to non-vascular (not of the smooth muscle cells surrounding a vessel) parenchymal cells.

In yet another preferred embodiment, a device for applying pressure to mammalian skin for in vivo delivery of a polynucleotide to a mammalian cell is described. The device consists of a cuff, as defined in this specification, applied to mammalian skin to impede blood flow thereby increasing delivery efficiency of the polynucleotide to the mammalian cell.

In a preferred embodiment it may be preferential to immunosuppress the host receiving the nucleic acid. Immunosuppression can be long term or for a short duration, preferably around the time of nucleic acid delivery. This can be accomplished by treatment with (combinations of) immunosuppressive drugs like cyclosporin A, ProGraf (FK506), corticosteroids, deoxyspergualin, and dexamethason. Other methods include blocking of immune cell activation pathways, for instance by treatment with (or expression of) an antibody directed against CTLA4; redirection of activated immune cells by treatment with (ore expression of) chemokines such as MIP-1α, MCP-1 and RANTES; and treatment with immunotoxins, such as a conjugate between anti-CD3 antibody and diphtheria toxin.

Further objects, features, and advantages of the invention will be apparent from the following detailed description when taken in conjunction with the accompanying drawings.

DETAILED DESCRIPTION

We have found that an intravascular route of administration allows a polynucleotide to be delivered to a parenchymal cell in a more even distribution than direct parenchymal injections. The efficiency of polynucleotide delivery and expression is increased by increasing the permeability of the tissue's blood vessel. Permeability is increased by one or more of the following: increasing the intravascular hydrostatic (physical) pressure, delivering the injection fluid rapidly (injecting the injection fluid rapidly), using a large injection volume, inhibiting vessel fluid flow, and increasing permeability of the vessel wall. Prior to insertion, subsequent to insertion, or concurrent with insertion the permeability of the vessel is increased using an exterior cuff thereby the genetic material is delivered to the parenchymal cell.

We describe a process for inserting a polynucleotide into mammalian cells. More particularly we have injected Rhesus macaque monkey limbs and caused the polynucleotide to be delivered and expressed. For both the arm and leg injections, blood flow was impeded by a cuff surrounding the arm or leg. The high luciferase and β-galactosidase levels achieved in monkeys indicate that the procedure is likely to be efficient in humans. It is noteworthy that expression levels were similar in monkeys as those levels in rats since the efficiency of many prior art gene transfer techniques is less in larger animals.

The term cuff means a device for impeding blood flow through mammalian internal blood vessels. However, for purposes of the claims, cuff refers specifically to a device applied exterior to the mammal's skin and touches the skin in a non-invasive manner. In a preferred embodiment, the cuff is a device that applies external pressure to the mammalian skin and thereby pressure is applied internally to the blood vessel walls. The vessel walls are forced to constrict in an area underneath the cuff in amount sufficient to impede blood from flowing at a normal rate. Impeding blood flow causes vascular pressure and vessel permeability to increase and the blood and its contents (including polynucleotides) are urged out of the vessel walls and into the extravascular space. One example of a cuff is a sphygmomanometer which is normally used to measure pressure. In a preferred embodiment of this specification, the sphygmomanometer is used to apply pressure to mammalian skin, around a limb, for the purpose of increasing vessel permeability. Another example is a tourniquet.

In yet another preferred embodiment the use of a cuff (or other external pressure device) is combined with the use of a pharmaceutical or biologically-active agent (such as papaverine) to increase vascular permeability.

The term intravascular refers to an intravascular route of administration that enables a polymer, oligonucleotide, or polynucleotide to be delivered to cells more evenly distributed than direct injections. Intravascular herein means within an internal tubular structure called a vessel that is connected to a tissue or organ within the body of an animal, including mammals. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

Afferent blood vessels of organs are defined as vessels in which blood flows toward the organ or tissue under normal physiologic conditions. Efferent blood vessels are defined as vessels in which blood flows away from the organ or tissue under normal physiologic conditions. In the heart, afferent vessels are known as coronary arteries, while efferent vessels are referred to as coronary veins.

The term naked nucleic acids indicates that the nucleic acids are not associated with a transfection reagent or other delivery vehicle that is required for the nucleic acid to be delivered to a target cell. A transfection reagent is a compound or compounds used in the prior art that mediates nucleic acid's entry into cells.

Additionally, a nucleic acid can be delivered to block gene expression. Such nucleic acids can be anti-sense by preventing translation of a messenger RNA or could block gene expression by preventing transcription of the gene. Preventing RNA translation and/or DNA transcription is considered preventing expression or RNA processing. Ribozymes can also be used to destroy cellular RNA. Transcription can be blocked by the nucleic acid binding to the gene as a duplex or triplex. It could also block expression by binding to proteins that are involved in a particular cellular biochemical process.

A polynucleotide may be a nucleic acid that recombines with chromosomal DNA.

Expression cassette refers to a natural or recombinantly produced nucleic acid which is capable of expressing protein (s). A DNA expression cassette typically includes a "promoter" (allowing transcription initiation), and a sequence encoding one or more proteins ("transgene(s)"). Optionally, the expression cassette may include transcriptional enhancers, locus control regions, matrix attachment regions, scaffold attachment regions, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

The expression cassette promoter can be selected from any of the known promoters isolated from the group consisting of, but not limited to, the human genome, mammalian genomes, microbial genomes, and chimeric sequences. Additionally, artificially constructed sequences can be used that have shown to have promoter activity in the target cell type. Examples of viral promoters that have successfully been used to express transgenes include: human cytomegalovirus immediate early promoter, Rous sarcoma virus, Moloney leukemia virus, and SV40. Examples of mammalian promoters include: elongation factor 1, muscle creatine kinase, actin, desmin, and troponin. The choice of promoter in conjunction with other expression cassette elements can determine the level of transgene protein production in target cells. The expression cassette can be designed to express preferentially in specific cell types (operationally defined as a 5-fold higher expression level in the specific cell type compared to the average expression level in other cell types). A promoter, or combination of a promoter and other regulatory elements in the expression cassette, resulting in preferential expression in specific cell types is frequently referred to as "tissue-specific." An example of a tissue-specific promoter is the muscle creatine kinase promoter, which expresses transgenes at high levels in skeletal muscle cells, whereas expression in other cell types is at lower levels. Preferential expression in muscle cells can be achieved by using promoters and regulatory elements from muscle-specific genes (e.g., muscle creatine kinase, myosin light chain, desmin, skeletal actin), or by combining transcriptional enhancers from muscle-specific genes with a promoter normally active in many cell types (e.g., the human cytomegalovirus immediate early promoter in combination with the myosin light chain enhancer).

Protein refers herein to a linear series of greater than 2 amino acid residues connected one to another as in a polypeptide. A therapeutic effect of the protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, interferons, enzymes (e.g. lysosomal enzymes), growth factors, clotting factors, anti-protease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein (e.g., low density lipoprotein receptor). Therapeutic proteins that stay within the cell ("intracellular proteins") can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, dystroglycans) and thus have a therapeutic effect in cardiomyopathies and musculoskeletal diseases (e.g., Duchenne muscular dystrophy, limb-girdle disease). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors.

Constructs to Improve Secretion of Muscle Expressed Protein Into the Blood

Proteins are targeted for secretion from cells by the presence of a signal peptide. During transit through the endoplasmic reticulum, the signal peptide is removed by specific proteolytic cleavage. It can be anticipated that secretion of certain proteins can be improved by replacing the endogenous signal peptide with a heterologous signal peptide. This can be accomplished by exchanging the coding regions for the signal peptides in the nucleic acid. For example, the signal from the protein placental alkaline phosphatase (often used in a truncated from as secreted alkaline phosphatase, SEAP) can be used to replace the signal from the protein factor IX. This may result in better secretion of the factor IX protein from muscle cells. Since the signal peptide is cleaved prior to secretion, the secreted mature factor IX protein is unaltered and functional. Alternatively, one can construct a fusion between the complete SEAP and target protein, or use other defined protein sequence known to enhance transmembrane transport, such as the TAT protein from the human immunodeficiency virus, or the VP22 protein from herpesviruses.

There are three types of "reporter" (or "marker") gene products that are expressed from reporter genes. The reporter gene/protein systems include:

Intracellular gene products such as luciferase, β-galactosidase, or chloramphenicol acetyl transferase. Typically, they are enzymes whose enzymatic activity can be easily measured. Intracellular gene products such as β-galactosidase or green fluorescent protein which identify cells expressing the reporter gene. On the basis of the intensity of cellular staining, these reporter gene products also yield qualitative information concerning the amount of foreign protein produced per cell.

Secreted gene products such as growth hormone, factor IX, secreted alkaline phosphatase, or alpha1-antitrypsin are useful for determining the amount of a secreted protein that a gene transfer procedure can produce. The reporter gene product can be assayed in a small amount of blood.

We have disclosed gene expression achieved from reporter genes in specific tissues. The terms "therapeutic" and "therapeutic results" are defined in this application as a nucleic acid which is transfected into a cell, in vivo, resulting in a gene product (e.g. protein) being expressed in the cell or secreted from the cell. Levels of a gene product, including reporter (marker) gene products, are measured which then indicate a reasonable expectation of similar amounts of gene expression by transfecting other nucleic acids. Levels of treatment considered beneficial by a person having ordinary skill in the art of gene therapy differ from disease to disease, for example: Hemophilia A and B are caused by deficiencies of the X-linked clotting factors VIII and IX, respectively. Their clinical course is greatly influenced by the percentage of normal serum levels of factor VIII or IX: <2%, severe; 2-5%, moderate; and 5-30% mild. This indicates that in severe patients an increase from 1% to 2% of the normal level can be considered beneficial. Levels greater than 6% prevent spontaneous bleeds but not those secondary to surgery or injury. A person having ordinary skill in the art of gene therapy would reasonably anticipate beneficial levels of expression of a gene specific for a disease based upon sufficient levels of marker gene results. In the hemophilia example, if marker genes were expressed to yield a protein at a level comparable in volume to 2% of the normal level of factor VIII, it can be reasonably expected that the gene coding for factor VIII would also be expressed at similar levels.

Parenchymal Cells

Parenchymal cells are the distinguishing cells of a gland or organ contained in and supported by the connective tissue framework. The parenchymal cells typically perform a function that is unique to the particular organ. The term "parenchymal" often excludes cells that are common to many organs and tissues such as fibroblasts and endothelial cells within blood vessels.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to an hepatic sinusoid and opposed sides to a bile canaliculus. Liver cells that are not parenchymal cells include cells within the blood vessels such as the endothelial cells or fibroblast cells. In one preferred embodiment hepatocytes are targeted by injecting the polynucleotide within the tail vein of a rodent such as a mouse.

In striated muscle, the parenchymal cells include myoblasts, satellite cells, myotubules, and myofibers. In cardiac muscle, the parenchymal cells include the myocardium also known as cardiac muscle fibers or cardiac muscle cells and the cells of the impulse connecting system such as those that constitute the sinoatrial node, atrioventricular node, and atrioventricular bundle. In one preferred embodiment striated muscle such as skeletal muscle or cardiac muscle is targeted by injecting the polynucleotide into the blood vessel supplying the tissue. In skeletal muscle an artery is the delivery vessel; in cardiac muscle, an artery or vein is used.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

One of our several methods of nucleic acid delivery to cells is the use of nucleic acid-polycations complexes. It was shown that cationic proteins like histones and protamines or synthetic polymers like polylysine, polyarginine, polyornithine, DEAE dextran, polybrene, and polyethylenimine are effective intracellular delivery agents while small polycations like spermine are ineffective.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers that contain equal amounts of anions and cations. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations.

In one embodiment, polycations are mixed with polynucleotides for intravascular delivery to a cell. Polycations provide the advantage of allowing attachment of DNA to the target cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis. Furthermore, polycations are a very convenient linker for attaching specific receptors to DNA and as result, DNA-polycation complexes can be targeted to specific cell types.

Additionally, polycations protect DNA in complexes against nuclease degradation. This is important for both extra- and intracellular preservation of DNA. The endocytic step in the intracellular uptake of DNA-polycation complexes is suggested by results in which DNA expression is only obtained by incorporating a mild hypertonic lysis step (either glycerol or DMSO). Gene expression is also enabled or increased by preventing endosome acidification with $NH_4Cl$ or chloroquine. Polyethylenimine which facilitates gene expression without additional treatments probably disrupts endosomal function itself. Disruption of endosomal function has also been accomplished by linking the polycation to endosomal-disruptive agents such as fusion peptides membrane active compounds, or adenoviruses.

Membrane Active Compounds

Many biologically active compounds, in particular large and/or charged compounds, are incapable of crossing biological membranes. In order for these compounds to enter cells, the cells must either take them up by endocytosis, into endosomes, or there must be a disruption of the cellular membrane to allow the compound to cross. In the case of endosomal entry, the endosomal membrane must be disrupted to allow for the entrance of the compound in the interior of the cell. Therefore, either entry pathway into the cell requires a disruption of the cellular membrane. There exist compounds termed membrane active compounds that disrupt membranes. One can imagine that if the membrane active agent were operative in a certain time and place it would facilitate the transport of the biologically active compound across the biological membrane. The control of when and where the membrane active compound is active is crucial to effective transport. If the membrane active compound is too active or active at the wrong time, then no transport occurs or transport is associated with cell rupture and thereby cell death. Nature has evolved various strategies to allow for membrane transport of biologically active compounds including membrane fusion and the use membrane active compounds whose activity is modulated such that activity assists transport without toxicity. Many lipid-based transport formulations rely on membrane fusion and some membrane active peptides' activities are modulated by pH. In particular, viral coat proteins are often pH-sensitive, inactive at neutral or basic pH and active under the acidic conditions found in the endosome.

Polycations also cause DNA condensation. The volume which one DNA molecule occupies in complex with polycations is drastically lower than the volume of a free DNA molecule. The size of DNA/polymer complex may be important for gene delivery in vivo. In terms of intravenous injection, DNA must cross the endothelial barrier and reach the parenchymal cells of interest.

The average diameter of liver fenestrae (holes in the endothelial barrier) is about 100 nm, and increases in pressure and/or permeability can increase the size of the fenestrae. The fenestrae size in other organs is usually less. The size of the DNA complexes is also important for the cellular uptake process. After binding to the target cells the DNA-polycation complex is expected to be taken up by endocytosis.

Polymers may incorporate compounds that increase their utility. These groups can be incorporated into monomers prior to polymer formation or attached to the polymer after its formation. The gene transfer enhancing signal (Signal) is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The gene transfer enhancing signal can be a protein, peptide, lipid, steroid, sugar, carbohydrate, nucleic acid or synthetic compound. The gene transfer enhancing signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large Tag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the gene with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Polynucleotides

The term nucleic acid is a term of art that refers to a string of at least two base-sugar-phosphate combinations. (A polynucleotide is distinguished from an oligonucleotide by containing more than 120 monomeric units.) Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus. Anti-sense is a polynucleotide that interferes with the function of DNA and/or RNA. The term nucleic acids-refers to a string of at least two base-sugar-phosphate combinations. Natural nucleic acids have a phosphate backbone, artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of an tRNA (transfer RNA), snRNA (small nuclear RNA), rRNA (ribosomal RNA), mRNA (messenger RNA), anti-sense RNA, and ribozymes. DNA may be in form plasmid DNA, viral DNA, linear DNA, or chromosomal DNA or derivatives of these groups. In addition these forms of DNA and RNA may be single, double, triple, or quadruple stranded. The term also includes PNAs (peptide nucleic acids), phosphorothioates, phosphorodiamidate morpholino and other variants of the phosphate backbone of native nucleic acids.

A polynucleotide can be delivered to a cell to express an exogenous nucleotide sequence, to inhibit, eliminate, augment, or alter expression of an endogenous nucleotide sequence, or to express a specific physiological characteristic not naturally associated with the cell. Polynucleotides may be coded to express a whole or partial protein, or may be antisense.

A delivered polynucleotide can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Vectors are polynucleic molecules originating from a virus, a plasmid, or the cell of a higher organism into which another nucleic fragment of appropriate size can be integrated; vectors typically introduce foreign DNA into host cells, where it can be reproduced. Examples are plasmids, cosmids, and yeast artificial chromosomes; vectors are often recombinant molecules containing DNA sequences from several sources. A vector includes a viral vector: for example, adenovirus; DNA; adenoassociated viral vectors (AAV) which are derived from adenoassociated viruses and are smaller than adenoviruses; and retrovirus (any virus in the family Retroviridae that has RNA as its nucleic acid and uses the enzyme reverse transcriptase to copy its genome into the DNA of the host cell's chromosome; examples include VSV G and retroviruses that contain components of lentivirus including HIV type viruses).

A vector is used in this specification to mean any DNA molecule which could include associate molecules to transfer DNA sequences into a cell for expression. Examples include naked DNA, non-viral DNA complexes (e.g. DNA plus polymers [cationic or anionic], DNA plus transfection enhancing compounds, and DNA plus amphipathic compounds) and viral particles.

A non-viral vector is defined as a vector that is not assembled within an eukaryotic cell including non-viral DNA/polymer complexes and DNA with transfection enhancing compounds.

Skin is the external covering of a mammalian body including the epidermis, the dermis, and the subcutaneous tissue.

Permeability

In another preferred embodiment, the permeability of the vessel is increased. Efficiency of polynucleotide delivery and expression was increased by increasing the permeability of a blood vessel within the target tissue. Permeability is defined here as the propensity for macromolecules such as polynucleotides to move through vessel walls and enter the extravascular space. One measure of permeability is the rate at which macromolecules move through the vessel wall and out of the vessel. Another measure of permeability is the lack of force that resists the movement of polynucleotides being delivered to leave the intravascular space.

To obstruct, in this specification, is to block or inhibit inflow or outflow of blood in a vessel. Rapid injection may be combined with obstructing the outflow to increase permeability. For example, an afferent vessel supplying an organ is rapidly injected and the efferent vessel draining the tissue is ligated transiently. The efferent vessel (also called the venous outflow or tract) draining outflow from the tissue is also partially or totally impeded for a period of time sufficient to allow delivery of a polynucleotide. In the reverse, an efferent is injected and an afferent vessel flow is impeded.

In another preferred embodiment, the intravascular pressure of a blood vessel is increased by increasing the osmotic pressure within the blood vessel. Typically, hypertonic solutions containing salts such as NaCl, sugars or polyols such as mannitol are used. Hypertonic means that the osmolarity of the injection solution is greater than physiologic osmolarity. Isotonic means that the osmolarity of the injection solution is the same as the physiological osmolarity (the tonicity or osmotic pressure of the solution is similar to that of blood). Hypertonic solutions have increased tonicity and osmotic pressure similar to the osmotic pressure of blood and cause cells to shrink.

In another preferred embodiment, the permeability of the blood vessel can also be increased by a biologically-active molecule. A biologically-active molecule is a protein or a simple chemical such as papaverine or histamine that increases the permeability of the vessel by causing a change in function, activity, or shape of cells within the vessel wall such as the endothelial or smooth muscle cells. Typically, biologically-active molecules interact with a specific receptor or enzyme or protein within the vascular cell to change the vessel's permeability. Biologically-active molecules include vascular permeability factor (VPF) which is also known as vascular endothelial growth factor (VEGF). Another type of biologically-active molecule can also increase permeability by changing the extracellular connective material. For example, an enzyme could digest the extracellular material and increase the number and size of the holes of the connective material. Another type of biologically-active molecule is a chelator that binds calcium and thereby increases the endothelium permeability.

In another embodiment a non-viral vector along with a polynucleotide is intravascularly injected in a large injection volume. The injection volume is dependent on the size of the animal to be injected and can be from 1.0 to 3.0 ml or greater for small animals (i.e. tail vein injections into mice). The injection volume for rats can be from 6 to 35 ml or greater. The injection volume for primates can be 70 to 200 ml or greater. The injection volumes in terms of ml/body weight can be 0.03 ml/g to 0.1 ml/g or greater.

The injection volume can also be related to the target tissue. For example, delivery of a non-viral vector with a polynucleotide to a limb can be aided by injecting a volume greater than 5 ml per rat limb or greater than 70 ml for a primate. The injection volumes in terms of ml/limb muscle are usually within the range of 0.6 to 1.8 ml/g of muscle but can be greater. In another example, delivery of a polynucleotide to liver in mice can be aided by injecting the non-viral vector—polynucleotide in an injection volume from 0.6 to 1.8 ml/g of liver or greater. In another preferred embodiment, delivering a polynucleotide—non-viral vector to a limb of a primate rhesus monkey, the complex can be in an injection volume from 0.6 to 1.8 ml/g of limb muscle or anywhere within this range.

In another embodiment the injection fluid is injected into a vessel rapidly. The speed of the injection is partially dependent on the volume to be injected, the size of the vessel to be injected into, and the size of the animal. In one embodiment the total injection volume (1-3 mls) can be injected from 5 to 15 seconds into the vascular system of mice. In another embodiment the total injection volume (6-35 mls) can be injected into the vascular system of rats from 20 to 7 seconds. In another embodiment the total injection volume (80-200 mls) can be injected into the vascular system of monkeys from 120 seconds or less.

In another embodiment a large injection volume is used and the rate of injection is varied. Injection rates of less than 0.012 ml per gram (animal weight) per second are used in this embodiment. In another embodiment injection rates of less than ml per gram (target tissue weight) per second are used for gene delivery to target organs. In another embodiment injection rates of less than 0.06 ml per gram (target tissue weight) per second are used for gene delivery into limb muscle and other muscles of primates.

Cleavable Polymers

A prerequisite for gene expression is that once DNA/polymer complexes have entered a cell the polynucleotide must be able to dissociate from the cationic polymer. This may occur within cytoplasmic vesicles (i.e. endosomes), in the cytoplasm, or the nucleus. We have developed bulk polymers prepared from disulfide bond containing co-monomers and cationic co-monomers to better facilitate this process. These polymers have been shown to condense polynucleotides, and to release the nucleotides after reduction of the disulfide bond. These polymers can be used to effectively complex with DNA and can also protect DNA from DNases during intravascular delivery to the liver and other organs. After internalization into the cells the polymers are reduced to monomers, effectively releasing the DNA, as a result of the stronger reducing conditions (glutathione) found in the cell. Negatively charged polymers can be fashioned in a similar manner, allowing the condensed nucleic acid particle (DNA+polycation) to be "recharged" with a cleavable anionic polymer resulting in a particle with a net negative charge that after reduction of disulfide bonds will release the polynucleic acid. The reduction potential of the disulfide bond in the reducible co-monomer can be adjusted by chemically altering the disulfide bonds environment. This will allow the construction of particles whose release characteristics can be tailored so that the polynucleic acid is released at the proper point in the delivery process.

pH Cleavable Polymers for Intracellular Compartment Release

A cellular transport step that has importance for gene transfer and drug delivery is that of release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Chemicals such as chloroquine, bafilomycin or Brefeldin A1. Chloroquine decreases the acidification of the endosomal and lysosomal compartments but also affects other cellular functions. Brefeldin A, an isoprenoid fungal metabolite, collapses reversibly the Golgi apparatus into the endoplasmic reticulum and the early endosomal compartment into the trans-Golgi network (TGN) to form tubules. Bafilomycin $A_1$, a macrolide antibiotic is a more specific inhibitor of endosomal acidification and vacuolar type $H^+$-ATPase than chloroquine. The ER-retaining signal (KDEL sequence) has been proposed to enhance delivery to the endoplasmic reticulum and prevent delivery to lysosomes.

To increase the stability of DNA particles in serum, we have added to positively-charged DNA-polycation particles polyanions that form a third layer in the DNA complex and make the particle negatively charged. To assist in the disruption of the DNA complexes, we have synthesized polymers that are cleaved in the acid conditions found in the endosome, pH 5-7. We also have reason to believe that cleavage of polymers in the DNA complexes in the endosome assists in endosome disruption and release of DNA into the cytoplasm.

There are two ways to cleave a polyion: cleavage of the polymer backbone resulting in smaller polyions or cleavage of the link between the polymer backbone and the ion containing groups resulting in small ionized molecules and a polymer. In either case, the interaction between the polyion and DNA is broken and the number of molecules in the endosome increases. This causes an osmotic shock to the endosomes and disrupts the endosomes. In the second case, if the polymer backbone is hydrophobic it may interact with the membrane of the endosome. Either effect may disrupt the endosome and thereby assist in release of DNA.

To construct cleavable polymers, one may attach the ions or polyions together with bonds that are inherently labile such as disulfide bonds, diols, diazo bonds, ester bonds, sulfone bonds, acetals, ketals, enol ethers, enol esters, imines, imminiums, and enamines Another approach is construct the polymer in such a way as to put reactive groups, i.e. electrophiles and nucleophiles, in close proximity so that reaction between the function groups is rapid. Examples include having carboxylic acid derivatives (acids, esters, amides) and alcohols, thiols, carboxylic acids or amines in the same molecule reacting together to make esters, thiol esters, acid anhydrides or amides.

The present invention additionally provides for the use of polymers containing silicon-nitrogen (silazanes) linkages (either in the main chain of the polymer or in a side chain of the polymer) that are susceptible to hydrolysis. Hydrolysis of a silazane leads to the formation of a silanol and an amine. Silazanes are inherently more susceptible to hydrolysis than is the silicon-oxygen-carbon linkage, however, the rate of hydrolysis is increased under acidic conditions. The substitution on both the silicon atom and the amine can affect the rate of hydrolysis due to steric and electronic effects. This allows for the possibility of tuning the rate of hydrolysis of the silazane by changing the substitution on either the silicon or the amine to facilitate the desired affect.

In one embodiment, ester acids and amide acids that are labile in acidic environments (pH less than 7, greater than 4) to form an alcohol and amine and an anhydride are use in a variety of molecules and polymers that include peptides, lipids, and multimolecular associations such as liposomes.

In one embodiment, ketals that are labile in acidic environments (pH less than 7, greater than 4) to form a diol and a ketone are use in a variety of molecules and polymers that include peptides, lipids, and liposomes.

In one embodiment, acetals that are labile in acidic environments (pH less than 7, greater than 4) to form a diol and an aldehyde are use in a variety of molecules and polymers that include peptides, lipids, and liposomes.

In one embodiment, enols that are labile in acidic environments (pH less than 7, greater than 4) to form a ketone and an alcohol are use in a variety of molecules and polymers that include peptides, lipids, and liposomes.

In one embodiment, iminiums that are labile in acidic environments (pH less than 7, greater than 4) to form an amine and an aldehyde or a ketone are use in a variety of molecules and polymers that include peptides, lipids, and liposomes.

pH-Sensitive Cleavage of Peptides and Polypeptides:

In one embodiment, peptides and polypeptides (both referred to as peptides) are modified by an anhydride. The amine (lysine), alcohol (serine, threonine, tyrosine), and thiol (cysteine) groups of the peptides are modified by the an anhydride to produce an amide, ester or thioester acid. In the acidic environment of the internal vesicles (pH less than 6.5, greater than 4.5) (early endosomes, late endosomes, or lysosome) the amide, ester, or thioester is cleaved displaying the original amine, alcohol, or thiol group and the anhydride.

A variety of endosomolytic and amphipathic peptides can be used in this embodiment. A positively-charged amphipathic/endosomolytic peptide is converted to a negatively-charged peptide by reaction with the anhydrides to form the amide acids and this compound is then complexed with a polycation-condensed nucleic acid. After entry into the endosomes, the amide acid is cleaved and the peptide becomes positively charged and is no longer complexed with the polycation-condensed nucleic acid and becomes amphipathic and endosomolytic. In one embodiment the peptides contains tyrosines and lysines. In yet another embodiment, the hydrophobic part of the peptide (after cleavage of the ester acid) is at one end of the peptide and the hydrophilic part (e.g. negatively charged after cleavage) is at another end. The hydrophobic part could be modified with a dimethylmaleic anhydride and the hydrophilic part could be modified with a citranconyl anhydride. Since the dimethylmaleyl group is cleaved more rapidly than the citrconyl group, the hydrophobic part forms first. In another embodiment the hydrophilic part forms alpha helixes or coil-coil structures.

pH-Sensitive Cleavage of Lipids and Liposomes

In another embodiment, the ester, amide or thioester acid is complexed with lipids and liposomes so that in acidic environments the lipids are modified and the liposome becomes disrupted, fusogenic or endosomolytic. The lipid diacylglycerol is reacted with an anhydride to form an ester acid. After acidification in an intracellular vesicle the diacylglycerol reforms and is very lipid bilayer disruptive and fusogenic.

Non-Cleavable Polymers

Many cationic polymers such as histone (H1, H2a, H2b, H3, H4, H5), HMG proteins, poly-L-lysine, polyethylenimine, protamine, and poly-histidine are used to compact polynucleic acids to help facilitate gene delivery in vitro and in vivo. A key for efficient gene delivery using prior art methods is that the non-cleavable cationic polymers (both in vitro and in vivo) must be present in a charge excess over the DNA so that the overall net charge of the DNA/polycation complex is positive. Conversely, using our tail vein injection process having non-cleavable cationic polymer/DNA complexes we found that gene expression is most efficient when the overall net charge of the complexes are negative (DNA negative charge>polycation positive charge). Tail vein injections using cationic polymers commonly used for DNA condensation and in vitro gene delivery revealed that high gene expression occurred when the net charge of the complexes were negative.

EXAMPLES

The high luciferase and β-galactosidase levels achieved in monkeys indicate that the procedure is likely to be efficient in humans. Expression levels were somewhat higher in monkeys than in rats.

The intraarterial procedure requires that blood flow be impeded for substantially less than the couple of hours of ischemia required for tissue damage. In fact, a common anesthesia for human limb surgery (e.g., carpal tunnel repair) involves the blockage of blood flow for over one hour. We have not observed any widespread histologic evidence of ischemic muscle damage in rats or primates following the injections. The minimal elevations of muscle-derived enzymes in the serum also argues against any consequential muscle damage.

Given that ~150 ml of fluid is administered to ~10 kg animals, the large amount of fluid could adversely affect the animals cardiovascular or hemodynamic status. However, no adverse effects on the animals were observed.

The intravascular pressure can be damaging to the arteries. We have observed minimal intimal changes in the arteries that are presumed to be transient and without consequence. Nonetheless, this minimal arterial damage may be prevented by better controlling the intravascular pressure.

For this pDNA administration procedure, several factors limit expression to the non-target tissue. 1) The tourniquet prevents the immediate spread of vector outside of the limb. 2) efficient pDNA expression in the non-vascular parenchymal cells requires extravasation of the injected pDNA.

The procedure requires relatively large amounts of pDNA to be administered. This has not been associated with any toxic effects in rodents or monkeys. Given that the tourniquet delays pDNA distribution outside of the limb and the intravascular pDNA is rapidly degraded by circulating DNases, pDNA toxicity is unlikely. In addition, the cost for producing clinical grade pDNA is considerably less expensive than viral vectors and does not represent an obstacle to its clinical use.

Example 1

Intraarterial Injections in Monkeys

Seven Rhesus macaque monkeys (5 males; 2 females) of 6 to 13.7 kg body weight underwent intraarterial injections in their limbs following anesthesia with ketamine and halothane. For the forearm injections, a longitudinal incision, ~3 cm in length, was made on the skin along the inside edge of the biceps brachii and 2 cm above the elbow. After separating the artery from surrounding tissues and veins, a 20 g catheter was inserted into the brachial artery anterogradely and ligated in place. For the lower leg injections, the procedure was essentially the same as that used in the arm, but the incision was located on the upper edge of the popliteal fossae and the 20 g catheter was inserted into the popliteal artery.

For both the arm and leg injections, blood flow was impeded by a sphygmomanometer cuff surrounding the arm or leg proximal to the injection site. After the sphygmomanometer was inflated to more than 300 mmHg air pressure, the catheterized vessels were injected with 30 ml of normal saline containing 5 mg papaverine (Sigma Co.). Five min. later, a saline solution containing 100 µg pDNA/ml solution was rapidly injected within 30 to 45 sec. For the arms, the volume of each injection was 75 ml and 90 ml in the first two animals and 120 ml thereafter. The injection volume was ~180 ml for the lower legs. The DNA solutions were injected using a nitrogen-pressurized cylinder. Two min after injection, the catheters were removed and the sphygmomanometer deflated.

The procedure was initially done on four monkeys in which one arm and leg was injected and muscle biopsies were taken at one (#1-3) or two weeks (#4). Monkey #2 had to be sacrificed at two weeks after injection because of an eye infection (unrelated to our procedure). Three more monkeys (#5-7) received an injection in all four extremities (one arm and leg on one day and the other two extremities two days later). Muscle biopsies were obtained at one week and the animals were sacrificed at two weeks after the injections. In monkeys #6 and #7, an arm and leg were injected with pCI-LacZ; all other injections were with pCI-Luc+.

Example 2

Reporter Gene Systems

The pCI-Luc+ (Promega, Madison, Wis.) and pCI-LacZ plasmids express a cytoplasmic luciferase and the *Escherichia coli* LacZ, respectively, from the human cytomegalovirus (CMV) immediate-early promoter. The pCI vector (Promega) also contains an SV40 polyadenylation signal. pMI-Luc+ was constructed by replacing the CMV promoter in pCI-Luc+ with a 3300-bp murine muscle creatine kinase promoter. The vector pEBFP-N1 expresses a nuclear-localizing, blue-shifted green fluorescent protein (GFP) from the CMV promoter (Clontech, Palo Alto, Calif.).

Luciferase assays were performed on muscle biopsies, entire muscles and various tissues as previously reported. The relative light units (RLU) were converted to nanograms of luciferase by using luciferase standards (Molecular Probes, Eugene, Oreg.) and a standard curve in which luciferase protein (pg)=RLU×$5.1\times10^{-5}$.

For the β-galactosidase assays, muscle samples were taken from the proximal, middle, and distal positions of each muscle, cut into small pieces, frozen in cold isopentane, and stored at −80° C. Muscle pieces were randomly chosen from each muscle sample (for every position) and 10 µm-thick cryostat sections were made. Every tenth section, for a total of 20 sections, was stained and analyzed. The sections were incubated in X-gal staining solution (5 mM potassium ferricyanide, 5 mM potassium ferrocyanide, 1 mM magnesium chloride, 1 mM X-gal in 0.1 M PBS, pH 7.6) for 4-8 hours at room temperature and counterstained with hematoxylin and eosin. Three sections were selected randomly from the 20 sections of each position (usually the 4th, 11th and 17th sections, but an adjacent section was used if these sections were not intact). As previously described, the number of β-galactosidase-positive and total cells were determined within a cross area in each section by moving the counter grid from the top edge of the section to the bottom and from the left edge to the right. The percentage of β-galactosidase-positive cells for each muscle was gotten from the result of positive number divided by total cell number. A weighted average for the percent of transfected cells for each extremity muscle was determined as follows: (ΣAi*Mi)/M where Ai is percent of transfected cells for one muscle, Mi—weight of that muscle and M—whole weight of all muscles.

For the co-localization of β-galactosidase and GFP expression, 10 µm-thick cryostat sections were fixed with 4% formaldehyde for 5-10 min. Mouse-anti-β-galadosidase antibody and TRITC-labeled goat-anti-mouse IgG (Sigma) were used as primary and secondary antibodies, respectively. Using a Nikon Optiphot epifluorescence microscope with a SenSys CCD Camera (Photometrics, Tucson, Ariz.), two images were collected from the same view for TRITC-labeled β-galactosidase and for GFP and merged together using the program Adobe Photoshop 4.0.

Example 3

Luciferase and β-Galactosidase Expression

Seven rhesus macaque (6-20 years old) received pDNA injections into their limb arteries. All seven monkeys tolerated the procedure well and had full function of their arms, hands, legs and feet following the procedure. In particular, this indicates lack of damage to the radial nerve, which could have been sensitive to the inflated sphygmomanometer surrounding the upper arm. Swelling in the target limbs, a putative correlate of successful gene transfer, was noted afterwards but completely subsided by the next day. When the monkeys awakened from the anesthesia 15 to 30 min after the procedure, they did not appear to be in any discomfort beyond that of normal surgical recovery. Occasionally, the skin in the target limb had some spots of hemorrhage that resolved within several days.

Four of the monkeys were sacrificed at 14 to 16 days after injection and all the target muscles of their limbs were assessed for either luciferase or β-galactosidase expression (Table 1). These results indicate that the intraartery injection of pCI-Luc+ DNA yielded levels of luciferase expression in all muscles of forearm, hand, lower leg and foot, ranging from 345 to 7332 ng/g muscle (Table 1). The variability in luciferase expression in arm muscles for different animals appears dependent upon whether the tip of the catheter was positioned in the radial or ulnar artery. The average luciferase expression levels in the limb muscles were 991.5±187 ng/g for the arm and 1186±673 ng/g for the leg.

Figure 1:
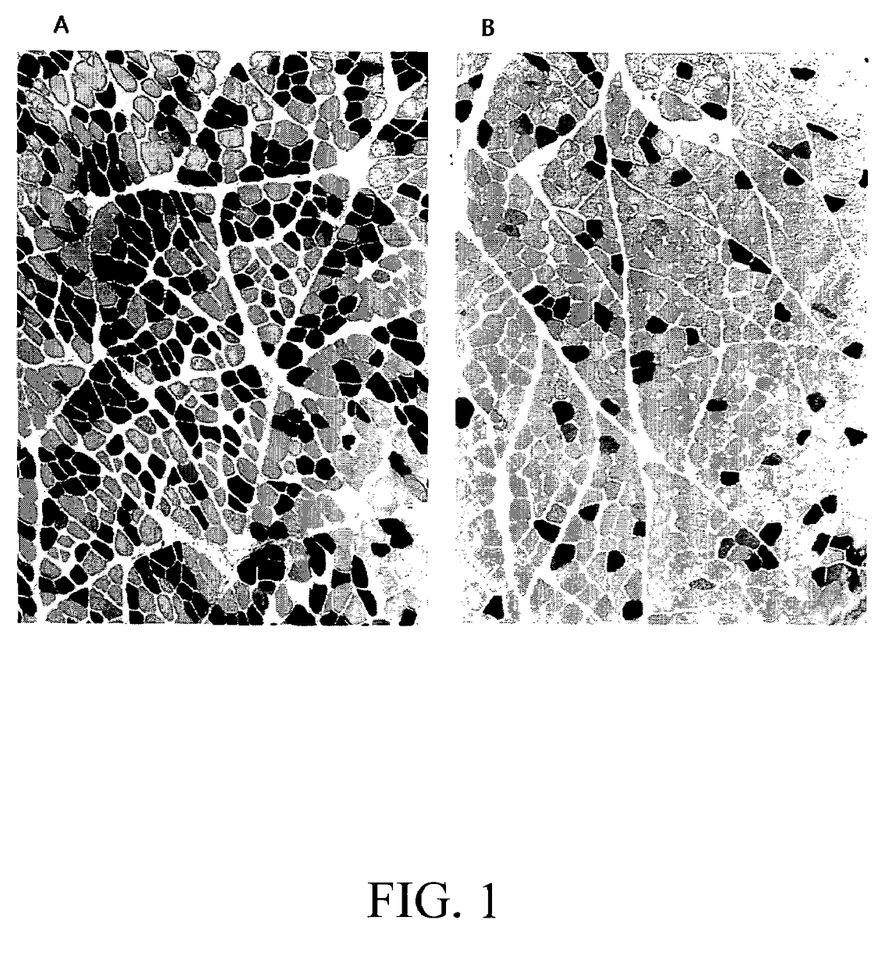
FIGS. 1A & 1B Photomicrographs of muscle sections histochemically stained for β-galactosidase expression. Panel A represents a muscle (pronator teres) with a high level of expression; panel B represents a muscle (abductor pollicis longus) with an average level of expression. Magnification: 160×.

After intraarterial injection of pCI-LacZ DNA, β-galactosidase expression was found in myofibers. Large numbers of β-galactosidase-positive myofibers were found in both leg and arm muscles, ranging from less than 1% to more than 30% in different muscles (Table 1 and FIG. 1). The average percentage for all four limbs injected was 7.4%, ranging from 6.3% to 9.9% for each of the limbs. The β-galactosidase percentages for specific muscle groups positively correlated with the luciferase levels in the same muscles (r=0.79).

TABLE 1

Mean muscle β-galactosidase or luciferase expression in four muscles from monkeys sacrificed two weeks after injection of pCI-LacZ or pCI-Luc+. "±" indicates standard error; n indicates the number of limbs assayed.

| Muscle group | | Muscle name | β-galactosidase (% positive) (n = 2) | Luciferase (ng/g muscle) (n = 5) |
|---|---|---|---|---|
| A. Arm muscles | | | | |
| Anterior group | Superficial group | palmaris longus | 5.9 ± 0.9 | 2368 ± 1309 |
| | | pronator teres | 19.9 ± 9.4 | 1818 ± 336 |
| | | flexor carpi radialis | 7.8 ± 0.7 | 1885 ± 762 |
| | | flexor carpi ulnaris | 3.8 ± 3.0 | 852 ± 314 |
| | | flexor digitorum spf. | 7.7 ± 1.2 | 1009 ± 189 |
| | Deep group | flexor digitorum prof. | 1.0 ± 0.5 | 544 ± 360 |
| | | pronator quatratus | 14.3 ± 11.1 | 1884 ± 331 |
| Posterior group | Superficial group | brachioradialis | 9.0 ± 8.7 | 1148 ± 942 |
| | | extensor carpi radialis longus | 6.6 ± 6.3 | 1179 ± 584 |
| | | extensor carpi radialis brevis | 9.4 ± 4.5 | 1118 ± 325 |
| | | extensor digitorum | 6.2 ± 5.4 | 1184 ± 94 |
| | | anconeus | 2.0 ± 0.3 | 1744 ± 372 |
| | | extensor carpi ulnaris | 0.6 ± 0.4 | 371 ± 86 |
| | | extensor pollicis longis | 6.9 ± 4.3 | 927 ± 228 |
| | Deep group | supinator | 15.1 ± 9.3 | 2398 ± 748 |
| | | abductor pollicis longus | 6.2 ± 3.8 | 927 ± 228 |
| | | extensor digiti secund et teriti | 6.0 ± 5.5 | 642 ± 168 |

TABLE 1-continued

Mean muscle β-galactosidase or luciferase expression in four muscles from monkeys sacrificed two weeks after injection of pCI-LacZ or pCI-Luc+. "±" indicates standard error; n indicates the number of limbs assayed.

| Muscle group | | Muscle name | β-galactosidase (% positive) (n = 2) | Luciferase (ng/g muscle) (n = 5) |
|---|---|---|---|---|
| | | A. Arm muscles | | |
| Muscles of hand | | extensor digiti quart et minimi | 4.0 ± 3.5 | 593 ± 140 |
| | | muscle of thumb | 15.7 ± 0.5 | 904 ± 494 |
| | | interosseus | 17.4 ± 4.3 | 1974 ± 185 |
| Weighted Average | | | 6.3 ± 0.04 | 991 ± 187 |
| | | B. Leg muscles | | |
| Posterior group | Superficial group | gastrocnemius | 3.0 ± 2.5 | 743 ± 33 |
| | | soleus | 21.2 ± 1.4 | 2888 ± 2151 |
| | Deep group | popliteus | 37.1 ± 0.5 | 4423 ± 2657 |
| | | flexor digitorum longus | 8.9 ± 2.4 | 3504 ± 2151 |
| | | flexor hallucis longus | 9.7 ± 2.4 | 1355 ± 1224 |
| | | tibialis posterior | 28.7 ± 4.3 | 7332 ± 5117 |
| Anterior group | | tibialis anterior | 2.8 ± 0.2 | 716 ± 162 |
| | | extensor hallucis longus | 4.2 ± 1.4 | 810 ± 497 |
| | | extensor digitorum longus | 10.9 ± 1.0 | 3187 ± 1166 |
| | | abductor hallucis longus | 2.2 ± 0.2 | 345 ± 104 |
| Internal group | | peronaus longus | 6.3 ± 2.5 | 626 ± 383 |
| | | peronaus brevis | 8.9 ± 1.3 | 1300 ± 23 |
| Muscles of foot | | extensor digitorum brevis | 6.2 ± 5.0 | 672 ± 607 |
| | | extensor hallucis brevis | 2.4 ± 1.8 | 672 ± 607 |
| LEG MUSCLES Weighted Average | | | 7.3 ± 0.1 | 1692 ± 768 |

Example 4

Toxicity

Serum chemistries and histologic analyses were performed to determine if the procedure caused any adverse effects in the monkeys. The serum levels of creatine phosphate kinase (CK), alanine aminotransferase, aspartate aminotransferase (AST) and lactate dehydrogenase (LDH) after surgery were several times higher than before surgery. Levels peaked at 48 hours post-injection and returning to normal within several days. Other serum enzymes such as γ-glutamyltransferase (GGT) and alkaline phosphatase, hematologic assays (hematocrit and RBC indices, platelets), serum electrolytes (Na, Cl, K), serum minerals (calcium, phosphate, iron), serum proteins (albumin, total protein), serum lipids (cholesterol, triglycerides), renal indices (urea, creatinine), and bilirubin were unaffected. Total WBC increased within the typical range post-surgery.

Limb muscles were obtained 14 to 16 days after intraarterial injection and examined histologically. The vast majority of muscle tissue was well preserved and did not show any sign of pathology. In a few sections, mononuclear cells were noted surrounding β-galactosidase positive myofibers, some of which were undergoing degeneration. Immunostaining for CD-markers indicated that the majority of infiltrating cells were CD3-positive (T lymphocytes) with only a few B cells.

Example 5

Timecourse of Muscle Expression After Intravascular Injection in Rats

Muscle luciferase expression was measured at several time points following intravascular delivery of the luciferase gene under control of either the CMV promoter (pCI-Luc$^+$) or MCK promoter (pMI-Luc$^+$) into: a) untreated rats, b) rats continuously immunosuppressed (treated with 2.5 mg/kg of FK506 orally and 1 mg/kg dexamethasone subcutaneously one day prior to, one hour prior to and every day thereafter with FK506) or c) transiently immunosuppressed (treated with 10 mg/kg of FK506 orally and 1 mg/kg dexamethasone subcutaneously one day prior to, one hour prior to and one day after intraarterial delivery of pDNA) (Table 2). In untreated rats, luciferase expression was lost after 7 days from the CMV promoter or after 21 days from the MCK promoter. In either pCI-Luc$^+$ or pMI-Luc$^+$ injected rats, anti-luciferase antibodies were detected using ELISA by day 21 and were present at higher levels at day 56 and 70 after intravascular pDNA delivery (data not shown).

TABLE 2

Time course of luciferase expression (ng/g muscle) in hindlimbs following intraarterial injections with 500 µg of pCI-Luc+ (A) or pMI-Luc+ (B) into rats treated with various immunosuppression regimens.

| | CONDITION | | |
|---|---|---|---|
| Time After Injection (Days) | No Treatment | Transient Immunno-suppression | Continuous Immunnosuppression |
| A. pCI-Luc+ | | | |
| 2 | 990.9 | | |
| 7 | 492.6 | | |
| 21 | 22.1 | | |
| 30 | 10.3 | 672.0 | 1212.0 |
| 56 | 0.3 | | |
| 70 | 0.1 | 17.3 | 464.0 |
| B. pMI-Luc+ | | | |
| 2 | 37.3 | | |
| 7 | 499.9 | | |
| 21 | 286.9 | | |
| 30 | | 1260.0 | |
| 56 | 3.3 | | |
| 70 | 0.3 | 571.0 | 1140.0 HERE |

Example 6

Repetitive Injections

Sprague-Dawley rats (150 g) were injected intaarterially in the right leg using 500 µg of pCI-Luc$^+$ under increased pressure conditions on day 0. On days 7 and 14 the rats were injected slowly with 300 µg pCI-Luc$^+$ in 1 ml into the tail vein. On day 24, the left leg was injected intraarterially with 500 µg of pCI-Luc$^+$. On day 26, the animals were sacrificed and the left leg revealed luciferase expression (mean=4,500 ng of total luciferase/leg muscles, n=2) similar to the levels achieved in animals not pre-injected with pDNA (mean=6,940 ng/leg muscles, n=26).

Figure 2:
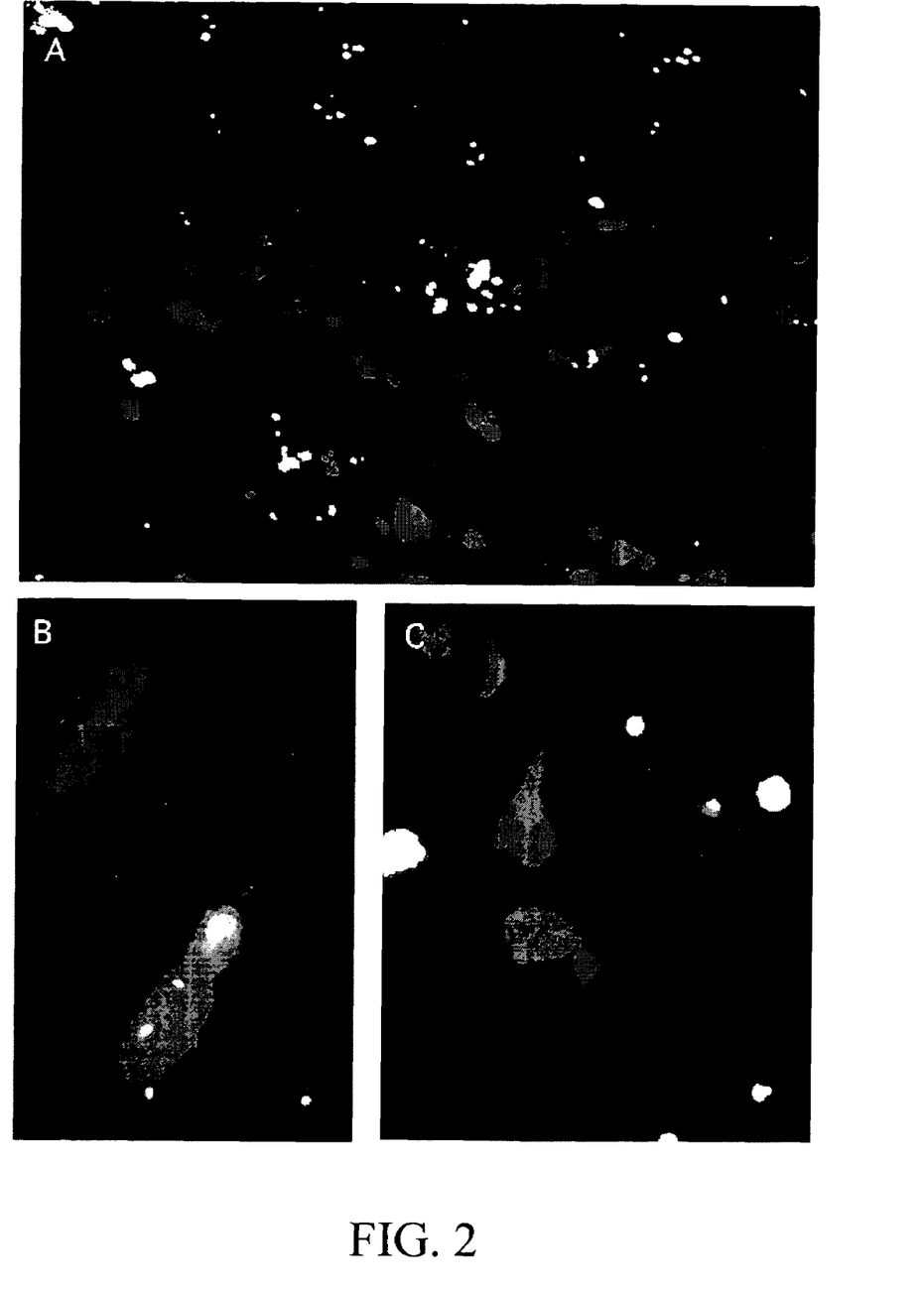
FIGS. 2A-2C Expression of β-galactosidase (light grey) and GFP (white) in rat muscle injected intraarterially at different times with the respective expression pDNAs. Panel A (640× magnification) is a low-power field illustrating that expression of β-galactosidase and GFP were typically not co-localized. Panels B and C are high power fields (1600× magnification) that show an example of co-localization (B) and separate expression (C).

In order to explore the ability to access different populations of myofibers, the same leg in rats were injected with the 500 µg of the β-galactosidase vector (pCI-LacZ) and two days hence with 500 µg of the nuclear GFP vector (pEBFP-N1). At two days after the last injection, the muscles were analyzed for expression of the two reporter genes. Expression of GFP and β-galactosidase was most often located in different myofibers (FIGS. 2A and C), but in some cells expression was coincident (FIG. 2B).

Example 7

Labeled pDNA Distribution in Muscle

Figure 3:
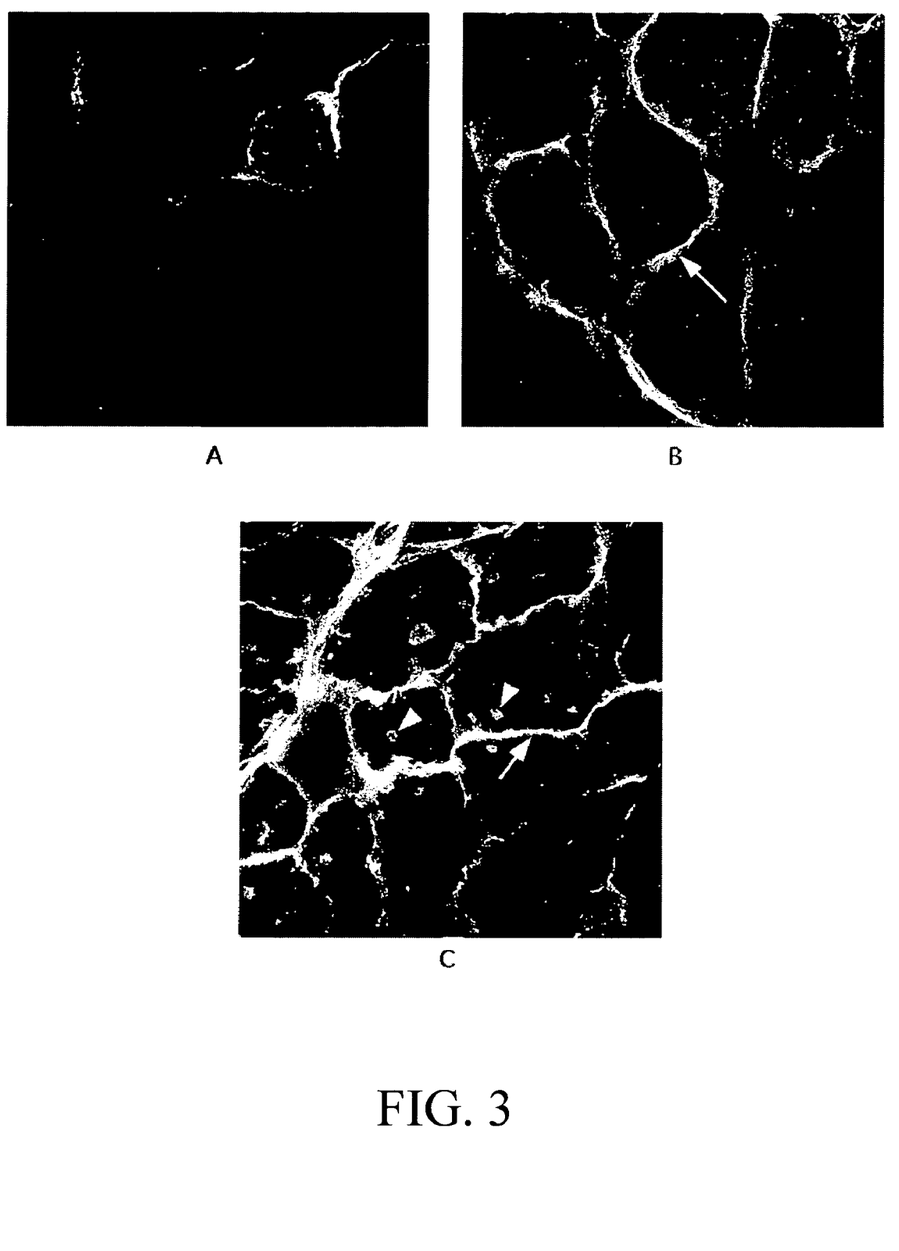
FIGS. 3A-3C Muscle sections obtained 5 min (A and B) and 1 h (C) after 50 μg of Rh-pDNA in 10 ml of normal saline were injected within 7 sec into the femoral artery of rat without impeding the outflow (A) or impeding outflow (B and C). Arrows indicate Rh-pDNA between cells and arrowheads indicate pDNA inside myofibers. Magnification: 260×.

Rhodamine-labeled pDNA (Rh-pDNA) was injected into the femoral artery of rats under various conditions in order to explore the uptake mechanism in muscle as was done for liver. When the injections were performed without impeding blood outflow (low intravascular pressure), almost no DNA was detected within the muscle tissues or vessels. FIG. 3A presents a rare field when some DNA can be seen between muscle cells. When the injections were performed with outflow occlusion (high intravascular pressure), Rh-pDNA was detected throughout all the muscle (FIGS. 3B and C). At 5 min after injection, examination of tissue sections indicated that the majority of the Rh-pDNA was surrounding the muscle cells and there was no intracellular staining (FIG. 3B, arrow). At one hour after injection, substantial amounts of DNA can be seen inside the cells (FIG. 3C, arrowhead). Examination of serial confocal sections indicates that the intracellular staining pattern is punctuate, unlikely consistent with a T tubular distribution.

Example 8

Expression of a Therapeutic Gene in Skeletal Muscle Tissue

A plasmid DNA (pCI-hF9) expressing the human factor IX gene (cDNA) under transcriptional control of the human cytomegalovirus promoter was delivered to rat hind limb skeletal muscle. A midline abdominal incision was made and skin flaps were folded away with clamps to expose target area. Intestines were moved to visualize the iliac veins and arteries. Microvessel clips were placed on the external iliac, caudal epigastric, internal iliac, deferent duct, and gluteal arteries and veins to block both outflow and inflow of the blood to the leg. An efflux enhancer solution (0.5 mg papaverine in 3 ml saline) was injected into the external iliac artery though a 25 g needle, followed by the pDNA containing solution (500 µg in 10 ml Ringer's) 5 minutes later. The pDNA solution was injected in approximately 10 seconds. The microvessel clips were removed 2 minutes after the injection, and the peritoneum and skin were closed using sutures. The rats were immunosuppressed by treatment with 10 mg/kg of FK506 orally and 1 mg/kg dexamethasone subcutaneously one day prior to, one hour prior to, and one day after plasmid DNA delivery The rats were sacrificed after 3 weeks, at which time the hind limb skeletal muscles were removed and homogenized in a total volume of 60 ml. Human factor IX levels in the rat sera were determined using an ELISA and compared to normal human serum. Expression levels in 3 rats were 1400, 1000, and 1150 ng/ml extract, respectively. Therefore, the total amount of human factor IX present in the rat muscle tissue three weeks after pDNA delivery was approximately 70 μg.

Example 9

Expression of Secreted Alkaline Phosphate from Rat Skeletal Muscle Cells

A plasmid DNA expression vector (pMIR54) was constructed in which the secreted alkaline phosphatase (SEAP) gene (obtained from plasmid pSEAP-2 basic, Clontech) is under transcriptional control of the human cytomegalovirus promoter. A solution of 500 μg pMIR54 in 10 ml Ringer's was injected into the iliac artery of Sprague Dawley rats as described in Examples above. The rats were immunosuppressed by treatment with 2.5 mg/kg of FK506 orally and 1 mg/kg dexamethasone subcutaneously one day prior to, one hour prior to plasmid DNA delivery. Following the pDNA delivery, the rats were treated with 2.5 mg/kg FK506 daily. Blood samples were obtained from these rats at several time points following plasmid DNA delivery. SEAP expression was determined using a chemiluminescent assay (Tropix) and compared to a standard curve.

|  | SEAP expression (ng SEAP per ml serum) | |
| --- | --- | --- |
|  | Day 7 | Day 14 |
| Rat 2889 | 2,301 | 1,407 |
| Rat 2992 | 3,735 | 2,942 |

Example 10

Expression in Multiple Muscle Groups

500 μg of pCI.Luc in 10 ml of normal saline solution was injected into the femoral artery of adult rats in which a tourniquet was applied to the outside of the leg proximal (tourniquet was applied to the upper portion of the quadriceps group of muscles) to the injection site. Five days after injection, the different muscle groups from the leg were removed and cut into equal sections. Each section was placed into lysis buffer, the muscles were homogenized and 10 ul of the resulting lysates were assayed for luciferase activity.

High levels of luciferase expression were expressed in all muscle groups that were located distal to the tourniquet. These included the biceps femoris, posterior muscles of the upper leg, gastrocnemius, muscles of the lower leg, and muscles of the plantar surface.

TABLE 3

Luciferase expression in the various muscles of the rat leg after the injection of 500 μg of pCILuc into the femoral artery with a tourniquet applied around the outside of the upper leg muscles.

| Muscle Group | Total Luciferase (ng/muscle group) |
| --- | --- |
| Intravascular Delivery to Rat Leg (with external tourniquet) | |
| Upper leg anterior (quadriceps) | 0.181* (*majority of this muscle group was above the tourniquet) |
| Upper leg middle (biceps femoris) | 28.3 |
| Upper leg posterior | 146 |

TABLE 3-continued

Luciferase expression in the various muscles of the rat leg after the injection of 500 μg of pCILuc into the femoral artery with a tourniquet applied around the outside of the upper leg muscles.

| Muscle Group | Total Luciferase (ng/muscle group) |
| --- | --- |
| (hamstrings) | |
| Lower leg posterior (gastrocnemius) | 253.6 |
| Lower leg anterior (lower shin muscles) | 115.2 |
| Muscles of the plantar surface | 0.433 |
| Intravascular Delivery to Rat Leg (without tourniquet) | |
| Upper leg anterior (quadriceps) | 0.010 |
| Upper leg middle (biceps femoris) | 0.011 |
| Upper leg posterior (hamstrings) | 2.16 |
| Lower leg posterior (gastrocnemius) | 1.57 |
| Lower leg anterior (lower shin muscles) | 0.72 |
| Muscles of the plantar surface | 0.202 |

Intravascularly-administered plasmid DNA is expressed efficiently in multiple muscle groups when blood flow is impeded using an external tourniquet.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. An in vivo process for delivering polynucleotides to skeletal muscle cells in a limb of a mammal, comprising:
   a) inserting an injector selected from the group consisting of a syringe needle and catheter into an artery in said limb;
   b) applying a device for impeding blood flow to the surface of the skin of said limb;
   c) applying sufficient pressure against said limb with said device to occlude blood flow to said limb; and,
   d) injecting a solution containing the polynucleotides through said injector into the lumen of said artery distal to the occlusion thereby delivering the polynucleotides to said skeletal muscle cells distal to said occlusion in the limb.

2. The process of claim 1 wherein the polynucleotide consists of naked DNA.

3. The process of claim 1 wherein the polynucleotide is selected from the group consisting of a viral vector and a non-viral vector.

4. The process of claim 1 wherein the muscle cell consists of a leg muscle cell.

5. The process of claim 1 wherein the muscle cell consists of an arm muscle cell.

6. The process of claim 5 wherein the arm muscle cell consists of an anterior muscle cell.

7. The process of claim 6 wherein the anterior muscle cell consists of an anterior superficial muscle cell.

8. The process of claim 7 wherein the muscle cell is selected from the group consisting of palmaris longus, pronator teres, flexor carpi radialis, flexor carpi ulnaris, and flexor digitorum superficialis.

9. The process of claim 6 wherein the anterior muscle cell is selected from the group consisting of flexor digitorum profundus, and pronator quadratus.

10. The process of claim 5 wherein the arm muscle cell consists of a posterior muscle cell.

11. The process of claim 10 wherein the posterior muscle cell consists of a posterior superficial muscle cell.

12. The process of claim 11 wherein the muscle cell is selected from the group consisting of brachioradialis, extensor carpi radialis longus, extensor carpi, radialis brevis, extensor digitorum, anconeus, extensor and carpi ulnaris.

13. The process of claim 10 wherein the posterior muscle cell is selected from the group consisting of supinator, extensor pollicis longus, abductor pollicis longus, extensor digiti secund et teriti, and extensor digiti quart et minimi.

14. The process of claim 5 wherein the arm muscle cell consists of a hand muscle cell.

15. The process of claim 14 wherein the hand muscle cell consists of a thumb muscle cell.

16. The process of claim 14 wherein the hand muscle cell consists of an interosseus cell.

17. The process of claim 4 wherein the leg muscle cell consists of a posterior muscle cell.

18. The process of claim 17 wherein the posterior muscle cell consists of a superficial cell.

19. The process of claim 18 wherein the superficial cell is selected from the group consisting of gastrocnemius and soleus.

20. The process of claim 17 wherein the posterior muscle cell is selected from the group consisting of popliteus, flexor digitorum longus, flexor hallucis longus, and tibialis posterior.

21. The process of claim 4 wherein the leg muscle cell consists of a anterior muscle cell.

22. The process of claim 4 wherein the leg muscle cell consists of a foot muscle cell.

23. The process of claim 21 wherein the anterior muscle cell is selected from the group consisting of tibialis anterior, extensor hallucis longus, extensor digitorum longus, and abductor hallucis longus.

24. The process of claim 4 wherein the leg muscle cell is selected from the group consisting of peronaus longus and peronaus brevis.

25. The process of claim 22 wherein the foot muscle cell is selected from the group consisting of extensor digitorum brevis and extensor hallucis brevis.

26. The process of claim 1 wherein said device for impeding blood flow consists of a tourniquet.

27. The process of claim 1 wherein said device for impeding blood flow consists of a cuff surrounding said limb.

28. The process of claim 27 wherein said device for impeding blood flow consists of a sphygmomanometer cuff.

29. An in vivo process for delivering polynucleotides to skeletal muscle cells in a limb of a mammal, comprising:
   a) inserting an injector selected from the group consisting of syringe needle and catheter into a blood vessel in said limb in the mammal and applying pressure to the blood vessel wherein the pressure occludes blood flow through said blood vessel and is applied to the skin of said limb by a device external to the skin of said mammal and;
   b) injecting a solution containing the polynucleotides into the lumen of said blood vessel distal to the occlusion thereby delivering the polynucleotides to said skeletal muscle cells in the limb distal to the occlusion; and,
   c) wherein function of the limb is not affected by inserting the injector, applying pressure to the vessel, and injecting the solution.

* * * * *